United States Patent
Fukutani et al.

(10) Patent No.: US 7,916,283 B2
(45) Date of Patent: Mar. 29, 2011

(54) BIOLOGICAL INFORMATION IMAGING APPARATUS, BIOLOGICAL INFORMATION ANALYZING METHOD, AND BIOLOGICAL INFORMATION IMAGING METHOD

(75) Inventors: Kazuhiko Fukutani, Yokohama (JP); Takao Nakajima, Ebina (JP); Yasufumi Asao, Atsugi (JP); Toru Den, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/876,336

(22) Filed: Sep. 7, 2010

(65) Prior Publication Data

US 2010/0331707 A1 Dec. 30, 2010

Related U.S. Application Data

(60) Division of application No. 12/204,445, filed on Sep. 4, 2008, which is a continuation of application No. PCT/JP2008/059093, filed on May 12, 2008.

(30) Foreign Application Priority Data

May 15, 2007 (JP) .................................. 2007-129890
Apr. 1, 2008 (JP) .................................. 2008-095126

(51) Int. Cl.
*G01N 21/00* (2006.01)
(52) U.S. Cl. ......................................... 356/73; 600/309
(58) Field of Classification Search .............. 356/72–73; 600/309–310
See application file for complete search history.

(56) References Cited

U.S. PATENT DOCUMENTS

| 4,385,634 A | 5/1983 | Bowen | 600/407 |
| 5,348,002 A | 9/1994 | Caro | 600/310 |
| 5,713,356 A | 2/1998 | Kruger | 600/407 |
| 5,746,211 A | 5/1998 | Leigh et al. | 600/407 |
| 5,840,023 A | 11/1998 | Oraevsky et al. | 600/407 |
| 6,070,093 A * | 5/2000 | Oosta et al. | 600/310 |
| 6,264,610 B1 | 7/2001 | Zhu | 600/443 |

(Continued)

FOREIGN PATENT DOCUMENTS

JP 06-296612 10/1994

(Continued)

OTHER PUBLICATIONS

A. P. Gibson et al., "Recent Advances in Diffuse Optical Imaging," Institute of Physics Publishing, *Physics in Medicine and Biology*, Phys. Med. Biol. 50 R1-R43 (2005).

(Continued)

*Primary Examiner* — Kara E Geisel
(74) *Attorney, Agent, or Firm* — Fizpatrick, Cella, Harper & Scinto

(57) ABSTRACT

A biological information imaging apparatus includes: a light source; an acoustic wave detector that detects an acoustic wave generated from a light absorption material in a living body that has absorbed a part of energy of light irradiated from the light source to the living body, and converts it into a first electric signal; a photodetector that detects optical intensity of a portion of the light irradiated from the light source to the living body and propagating in the living body, and converts it into a second electric signal; and a calculation unit that calculates optical property distribution information on the living body by making use of an analytical result of one of the first electric signal and the second electric signal for analysis of the other electric signal.

22 Claims, 6 Drawing Sheets

U.S. PATENT DOCUMENTS

| | | | |
|---|---|---|---|
| 2004/0127782 A1* | 7/2004 | Sfez et al. | 600/407 |
| 2005/0070803 A1 | 3/2005 | Cullum et al. | 600/473 |
| 2005/0187471 A1 | 8/2005 | Kanayama et al. | 600/437 |
| 2008/0306371 A1 | 12/2008 | Fukutani et al. | 600/407 |
| 2009/0002685 A1* | 1/2009 | Fukutani et al. | 356/72 |
| 2009/0198128 A1 | 8/2009 | Fukutani et al. | 600/437 |

FOREIGN PATENT DOCUMENTS

| | | |
|---|---|---|
| JP | 09-500566 | 1/1997 |
| WO | WO 2006/067699 | 6/2006 |
| WO | WO 2008/005554 A2 | 1/2008 |
| WO | WO 2008/067438 A2 | 6/2008 |

OTHER PUBLICATIONS

Minghua Xu et al., "Photoacoustic Imaging in Biomedicine," *Review of Scientific Instruments*, America Institute of Physics, 77, 041101 (2006).

B. W. Pogue et al., "High-Resolution Near-Infrared Tomographic Imaging Simulations of the Rat Cranium by Use of a Priori Magnetic Resonance Imaging Structural Information," *Optics Letters*, vol. 23, No. 21, pp. 1716-1718 (Nov. 1, 1998).

Xueyi Xie et al., "Photoascoustic Tomography and Molecular Fluorescence Imaging: Dual Modality Imaging of Small Animal Brain in Vivo," *Proceedings of SPIE*, vol. 5697, pp. 107-110, XP002491360 (Nov. 1, 2005).

Lu Yin et al., "Tomographic Imaging of Absolute Optical Absorption Coefficient in Turbid Media Using Combined Photoacoustic and Diffusing Light Measurements," *Optical Society of America*, vol. 32, No. 17, pp. 2556-2558, XP001507597 (Jul. 24, 2007).

Daniel Razansky et al., "Hybird Photoacoustic Fluorescence Molecular Tomography Using Finite-Element-Based Inversion," *Med. Phys.*, vol. 34, No. 11, pp. 4293-4301, XP012103208 (Oct. 19, 2007).

John Gamelin et al., "Investigation of Photoacoustic Guidance of Diffusive Optical Tomography," Proceedings of SPIE, vol. 6856, No. 1, pp. 68560V-1 through 68560V10, XP002491361 (Feb. 7, 2008).

Daniel Razansky et al., "Fluorescence Molecular Tomography Using A-Priori Photoacoustic Data," *Proceedings of SPIE*, vol. 6856, No. 1, pp. 685617-1 through 685617-9, XP002491362 (Feb. 7, 2008).

B.T. Cox et al., "Quantitative Photoacoustic Image Reconstruction for Molecular Imaging," *Proceedings of SPIE*, vol. 6086, No. 1, pp. 60861M-1 through 60861M-8, XP002491363 (Feb. 9, 2006).

\* cited by examiner

BIOLOGICAL INFORMATION IMAGING APPARATUS, BIOLOGICAL INFORMATION ANALYZING METHOD, AND BIOLOGICAL INFORMATION IMAGING METHOD

RELATED APPLICATIONS

This application is a divisional of patent application Ser. No. 12/204,445, filed Sep. 4, 2008, which is a continuation of International Application No. PCT/JP2008/059093, filed May 12, 2008, claims benefit of that application under 35 U.S.C. §120, and claims priority benefit under 35 U.S.C. §119 of Japanese Patent Applications Nos. 2007-129890, filed on May 15, 2007, and 2008-095126, filed on Apr. 1, 2008; the entire disclosure of each of the three mentioned applications is incorporated herein by reference.

BACKGROUND OF THE INVENTION

1. Field of the Invention

The present invention relates to a biological information imaging apparatus and a biological information analyzing method. Further, the present invention also relates to a biological information imaging method.

2. Description of the Related Art

In the medical field, there have been actively studied photo-imaging apparatuses which can obtain information in a living body by causing light irradiated from a light source such as a laser onto the living body be propagated therein, and by detecting the propagation light.

One such optical imaging technique is a technique of DOT (Diffuse Optical Tomography), called diffuse optical imaging, as described in a first non-patent document described below. Diffuse optical imaging is a technique in which light is irradiated onto a living body from a light source, and the extremely feeble or weak light propagated and diffused in the living body is detected by an optical detector of high sensitivity, whereby a distribution of optical characteristic values in the living body is imaged from the detection signal. The light, being irradiated from the light source and having passed through a relatively thick tissue of the living body, is strongly scattered, as a result of which it propagates in the tissue of the living body in a diffused manner while losing its wave nature such as straightness of light propagation. Therefore, the values of optical properties (absorption coefficient $\mu_a$, effective scattering coefficient $\mu_s'$, etc.) of the tissue of the living body can be obtained by optically measuring the intensity of such diffused light at multiple points and by processing the measured values by means of a computer. Furthermore, a compositional distribution of materials that constitute the tissue of the living body can be obtained by measuring those optical property values at different wavelengths.

On the other hand, an optical imaging technique other than DOT is PAT (Photoacoustic Tomography), called photoacoustic imaging. Photoacoustic imaging is a technique that calculates a distribution of optical property in a living body with high resolution by making use of a property of ultrasonic waves having a smaller amount of scattering in the living body as compared with light.

In this method, pulsed light generated from a light source is irradiated onto the living body so as to be propagated and diffused therein, and an acoustic wave generated from the tissue of the living body that has absorbed the energy of the pulsed light is detected. By performing mathematical processing on this detection signal, it is possible to obtain distributions of optical properties in the living body, in particular, an optical energy absorption density distribution. It is said that by using this photoacoustic imaging, an optical property distribution with high resolution can be obtained as compared with the above-mentioned diffuse optical imaging.

According to a second non-patent document described below, in photoacoustic imaging, the sound pressure P of an acoustic wave obtained from an absorber in a living body due to the light or optical absorption thereof is provided by the following expression (1):

$$P = \Gamma \cdot \mu_a \cdot \Phi \quad (1)$$

Here, $\Gamma$ is the Grüneisen coefficient, which is related to an elastic property, and is obtained by dividing the product of the isobaric volume expansion coefficient $\beta$ and the squared speed of sound c by the specific heat $C_p$; $\mu_a$ is the absorption coefficient of the absorber; and $\Phi$ is the amount of light irradiated onto the absorber.

Because it is known that $\Gamma$ takes a substantially constant value for a given tissue, it is possible to obtain the product of $\mu_a$ and $\Phi$, i.e., an optical energy absorption density distribution H, by measuring the change of the sound pressure P, which is the magnitude of the acoustic wave, by time sharing (see the mentioned second non-patent document).

[First Non-Patent Document]
A. P. Gibson, et al., "Recent Advances in Diffuse Optical Imaging", *Phys. Med. Biol.,* 50 (2005) R1-R43.

[Second Non-Patent Document]
M. Xu and L. V. Wang, "Photoacoustic Imaging in Biomedicine", *Review of Scientific Instruments,* 77, 041101 (2006).

SUMMARY OF THE INVENTION

The object of the present invention is to provide a novel biological information imaging apparatus, a novel biological information imaging method, and a novel biological information analyzing method.

According to a first aspect of the present invention, there is provided a biological information imaging apparatus comprising: a light source; an acoustic wave detector that detects an acoustic wave generated from a light absorption material in a living body that has absorbed a part of energy of light irradiated from the light source to the living body, and converts the acoustic wave into a first electric signal; a photodetector that detects optical intensity of a portion of the light irradiated from the light source to the living body and propagating in the living body, and converts the optical intensity into a second electric signal; and a signal processing unit that calculates optical property distribution information on the living body by making use of an analytical result of one of the first electric signal and the second electric signal for analysis of the other electric signal.

In addition, according to a second aspect of the present invention, there is provided a biological information analyzing method for analyzing electric signals that are obtained from an acoustic wave detector and a photodetector, wherein the acoustic wave detector detects an acoustic wave generated from a light absorption material in a living body that has absorbed a part of energy of light irradiated from a light source to the living body, and converts the acoustic wave into a first electric signal, and the photodetector detects optical intensity of a portion of the light irradiated from the light source to the living body and propagating in the living body, and converts the optical intensity into a second electric signal, the method comprising the steps of: calculating an optical property distribution of the living body by making use of an analytical result of one of the first electric signal and the second electric signal for analysis of the other electric signal.

Moreover, according to a third aspect of the present invention, there is provided a biological information imaging apparatus which includes: a light source; an acoustic wave detector that detects an acoustic wave generated from a light absorption material in a living body having absorbed a part of the energy of light irradiated from the light source to the living body, and converts it into a first electric signal; a photodetector that detects the optical intensity of a portion of the light irradiated from the light source to the living body and propagating in the living body, and converts it into a second electric signal; a first information processing unit that analyzes the first electric signal to obtain optical property distribution information on the living body; and a second information processing unit that analyzes the optical property distribution information obtained by the first information processing unit and the second electric signal to obtain optical property distribution information on the living body.

According to the present invention, a novel biological information imaging apparatus, a novel biological information imaging method, and a novel biological information analyzing method can be provided.

Further features of the present invention will become apparent from the following description of exemplary embodiments of the present invention when taken in conjunction with the attached drawings.

DESCRIPTION OF THE PREFERRED EMBODIMENTS

Figure 1:
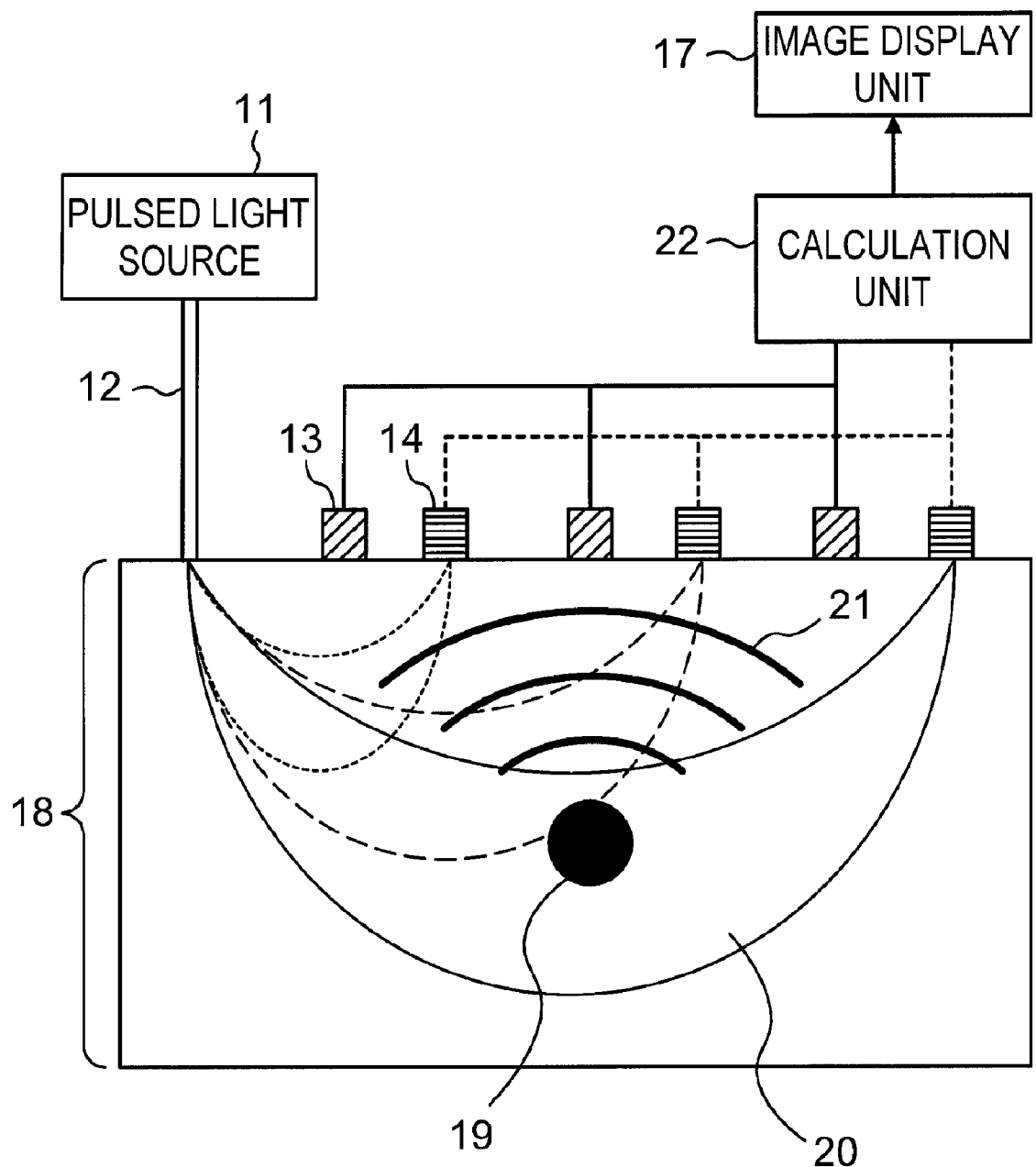
FIG. 1 is a view for explaining a constructional example of a biological information imaging apparatus in a first embodiment of the present invention.

A biological information imaging apparatus, a biological information imaging method, and a biological information analyzing method according to the present invention are characterized by making mutual use of data obtained by diffuse optical imaging (DOT) and data obtained by photoacoustic imaging (PAT) with each other.

Diffuse optical imaging and photoacoustic imaging are both techniques for obtaining distributions of absorption coefficients of absorbers existing in a living body. To this end, if diffuse optical imaging or photoacoustic imaging is to be combined with another imaging method, it is general to select an imaging method such as MRI (Magnetic Resonance Imaging), X-rays, etc., which is capable of obtaining information other than absorption coefficient distributions. In contrast to this, it can be said that the present invention is a novel imaging method conceived under a novel concept in terms of combining a plurality of techniques for obtaining absorption coefficient distributions with one another.

Specifically, ultrasonic waves are measured by means of photoacoustic imaging, and diffused light is measured by means of diffuse optical imaging, wherein an analytical result obtained by one of the photoacoustic imaging and the diffuse optical imaging is used for an analysis in the other imaging. The present inventors have found that the following, various advantageous effects can be achieved by combining the diffuse optical imaging and the photoacoustic imaging with each other in this manner.

(DOT: Diffuse Optical Imaging)

According to the above-mentioned diffuse optical imaging, it is possible to obtain a concentration distribution of materials that constitute a tissue of the living body, by measuring optical properties such as an absorption coefficient, etc.

However, in this diffuse optical imaging in which light is detected, the multiple scattering of light in a medium through which light is propagated, can be caused, so it is difficult to obtain high resolution images.

In addition, the diffuse optical imaging generally requires a long computing or calculation time for solving an ill-posed inverse problem or performing imaging by making comparison between detection results of a plurality of detectors for detecting diffused light and outputs of the individual detectors calculated from an optical diffusion equation.

Accordingly, when solving or calculating the ill-posed inverse problem, the imaging of the present invention uses optical property distribution information (e.g., absorption coefficient distribution) on an object that has been obtained beforehand by photoacoustic imaging. As a result, by applying such a constraint condition to the above-mentioned optical diffusion equation, a solution can be limited, thus making it possible to decrease the computing time required.

In addition, by limiting a region to be calculated based on the information obtained beforehand by the photoacoustic imaging, an amount of calculation or computational complexity for the above-mentioned optical diffusion equation can be reduced, thus making it possible to further decrease the computing time.

Further, if the information obtained by the photoacoustic imaging is used in the calculation of the inverse problem of light, it will be possible to obtain high-quality images that are higher in resolution than those obtained by ordinary optical diffusion imaging.

(PAT: Photoacoustic Imaging)

According to the above-mentioned photoacoustic imaging, scattering of acoustic waves in a living body is smaller in comparison with that of light, so the spatial information of the living body of a length less than a few millimeters can be obtained with high resolution.

In this photoacoustic imaging, as can be seen from equation (1) above, it is necessary to obtain a distribution ($\Phi$) of an amount of light irradiated onto the absorber by some methods so as to obtain a distribution of an absorption coefficient ($\mu_a$) in the living body from the measurement of a change in sound pressure (P).

However, in the case of the complex interior of the living body, there is a problem in that it is difficult to estimate the amount of light irradiated onto the absorber, and it is possible to image only an optical energy absorption density distribution ($\mu_a \cdot \Phi$) with the general sound intensity measurement of the acoustic wave alone. That is, it is difficult to calculate the distribution (Φ) of the amount of light irradiated onto the absorber only from the measurement of the acoustic wave alone, and to separate and image the distribution of the absorption coefficient ($\mu_a$) in the living body in an accurate manner.

As a result, there is a problem in that by means of the photoacoustic imaging alone, the accurate distribution of the absorption coefficient ($\mu_a$) cannot be obtained, thus making it impossible to specify the component materials of a tissue of the living body and to measure the concentrations thereof.

Accordingly, the imaging of the present invention can obtain the absorption coefficient used with photoacoustic imaging by using the data obtained according to diffuse optical imaging. Specifically, the amount of light (Φ) can be decided from the following optical diffusion equation approximation (one of light propagation model equations) independently of the ultrasonic measurement:

$$\frac{\partial \Phi(r, t)}{\partial t} = D\nabla^2 \Phi(r, t) - \nu \mu_a \Phi(r, t) + S_0(r, t) \quad D = \frac{\nu}{3\mu_s'}$$

Here, ∇ is differentiation with respect to space, $\mu_s'$ is an effective scattering coefficient, $\mu_a$ is an absorption coefficient, ν is the speed of light in the living body, and $S_0(r,t)$ is a light source term in the tissue.

That is, according to the diffuse optical imaging, the distribution of the amount of light (Φ), which could not be measured directly by photoacoustic imaging, can be directly decided. Therefore, with the imaging of the present invention, it is possible to obtain the quantitative absorption coefficient distribution with high resolution by making use of the amount of light (Φ) obtained by the diffuse optical imaging as well as the optical energy absorption density distribution ($\mu_a \cdot \Phi$) obtained by photoacoustic imaging.

Thus, the quantitativity and the resolution of the absorption coefficient distribution can be enhanced by the combined use of the photoacoustic imaging and the diffuse optical imaging. As a result, the concentrations of the materials that constitute the living body can be obtained. In addition, an accurate value of the distribution of the Grüneisen coefficient (Γ), which is treated as a constant in general photoacoustic imaging, can be obtained.

The above-mentioned principle will be described below by using FIG. 6A through FIG. 6C. FIG. 6A is a view showing one example of a specimen 62 of which the interior is imaged by means of an imaging technique using light. A light absorption material 63 exists in the interior of the specimen 62. A reference numeral 61 denotes light irradiated from a light source to the specimen 62, and the light absorption material 63 in the interior of the specimen 62 is imaged by using this light 61. Here, note that a reference numeral 64 denotes an absorption coefficient distribution in a dotted line portion of FIG. 6A. FIG. 6B shows an example of imaging the specimen of FIG. 6A by using a conventional photoacoustic imaging technique. A reference numeral 66 denotes a tomographic image, and 65 denotes an optical energy absorption density distribution ($\mu_a \cdot \Phi$) in a dotted line portion of FIG. 6B. As can be seen from FIG. 6B, an image of the optical energy absorption density distribution ($\mu_a \cdot \Phi$), which can be obtained by conventional photoacoustic imaging, is greatly different from an actual image of the absorption coefficient distribution ($\mu_a$). In other words, in the living body, etc., the amount of local light is attenuated greatly due to optical diffusion in proportion to the distance of light propagation, so even if the absorption coefficients and the sizes of two bodies of light absorption materials are the same, one of the light absorption materials, lying far away from a light irradiation region or light source, is imaged with lower contrast than the other light absorption material lying near the light irradiation region is.

Figure 6C:
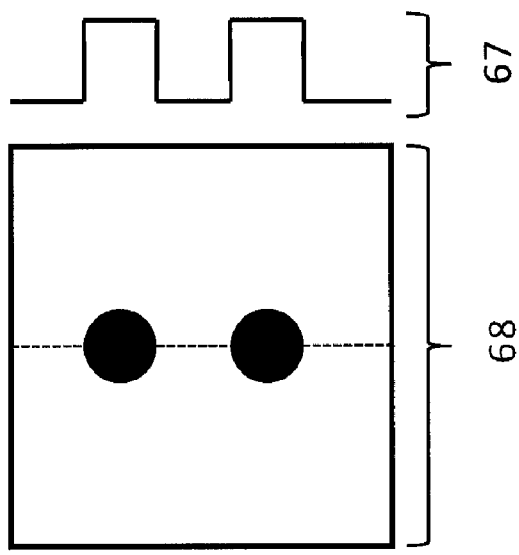
FIG. 6C is a view showing one example of an image obtained according to an imaging technique of the present invention.
Figure 6B:
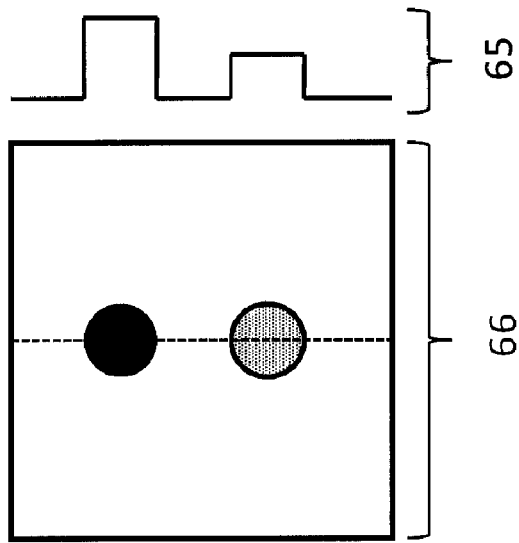
FIG. 6B is a view showing one example of an image obtained according to a conventional photoacoustic imaging technique.
Figure 6A:
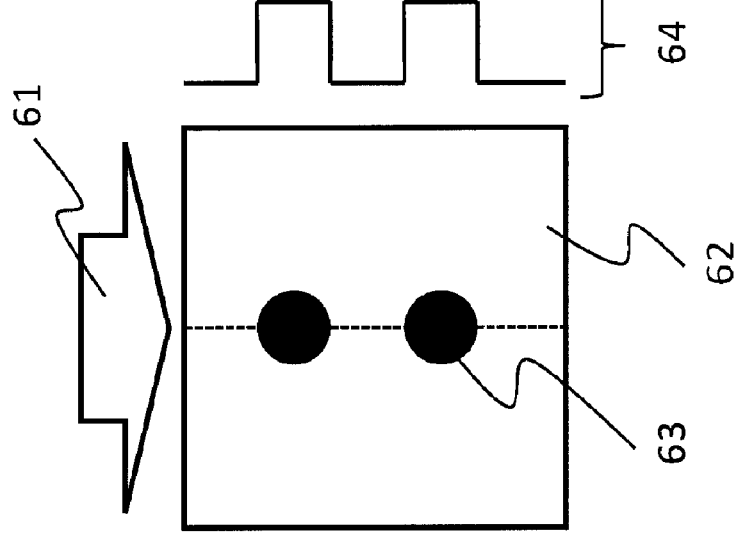
FIG. 6A is a view showing one example of a specimen to which an imaging technique using light is applied.

On the other hand, if the combined technique of photoacoustic imaging and diffuse optical imaging according to the present invention is used, an image as shown in FIG. 6C can be obtained. In FIG. 6C, a reference numeral 68 denotes a tomographic image, and 67 denotes an absorption coefficient distribution in a dotted-line portion of this figure. Thus, in the imaging of the present invention, light absorption materials having the same size and the same absorption coefficient can be imaged with substantially the same contrast even if they are far away from and near the light irradiation region or light source, respectively. In other words, an image of a light absorption material proportional to an actual absorption coefficient distribution thereof can be obtained.

(Image Reconstruction Algorithm)

Upon imaging, a comparison is made between the detection result of each photodetector obtained for example by a diffuse optical imaging apparatus and the result of calculation of the output at each detector obtained from the above-mentioned optical diffusion equation with its parameters estimated as stated above. If the results coincide with each other, the results are imaged or formed into an image.

On the other hand, when the results do not coincide with each other, an effective scattering coefficient distribution and an absorption coefficient distribution are assumed, the detection result in each detector is recalculated from the optical diffusion equation, and is compared again with the measurement result according to PAT.

It is possible to perform imaging by repeating the above-mentioned operations. Here, note that in comparison processing, coincidence between both of the results can be determined, of course, when the values of both results completely coincide with each other, or in addition, when a difference between the values of both results is within an allowable error range, which has been set beforehand.

In addition, when the image of an object is reconstructed, the following algorithm may be employed.

STEP 1) The size (d) and the position (x, y, z) of the absorber are decided by means of photoacoustic imaging.

STEP 2) The amount of light (Φ), the absorption coefficient ($\mu_a$) in each place, and the effective scattering coefficient ($\mu_s'$) are calculated according to the inverse problem calculation by using the size and position information acquired in STEP 1 by means of diffuse optical imaging.

STEP 3) The absorption coefficient ($\mu_a$) is calculated by using the above-mentioned amount of light (Φ) with respect to the result of photoacoustic imaging.

Now, preferred embodiments of the present invention will be described while referring to the accompanying drawings.

Embodiment 1

First, reference will be made to a biological information imaging apparatus according to a first embodiment of the present invention. FIG. 1 shows a view for explaining a constructional example of the biological information imaging apparatus of this first embodiment. The biological information imaging apparatus of this first embodiment serves to make it possible to provide the imaging of a distribution of optical properties or elastic properties in a living body as well as a concentration distribution of materials that constitute a tissue of the living body obtained from the distribution information in order to perform diagnoses on tumors such as a breast cancer, blood vessel diseases, etc., as well as observation of the progress of a chemical treatment or the like.

The biological information imaging apparatus of this embodiment is provided with a light source 11 for irradiating light to a living body 18, and an optical wave guide 12 for guiding the light irradiated from the light source 11 to the living body 18.

In addition, the biological information imaging apparatus is also provided with a plurality of acoustic wave detectors 13, each of which detects an acoustic wave 21, which a light absorption material 19 in the living body generates by absorbing a part of the optical energy of the light, and converts it into a first electric signal. The light absorption material 19 is a tumor, a blood vessel or the like.

Also, the biological information imaging apparatus is provided with a plurality of photodetectors 14, each of which detects the intensity of the light 20 after its diffusion in the living body, and converts it into a second electric signal.

Further, the biological information imaging apparatus is provided with a calculation unit 22 that obtains a first optical property distribution information by analyzing the first electric signals. The first optical property distribution information includes the size of the light absorption material, the position at which the light absorption material exists, a value related to the magnitude of a light absorption coefficient (e.g., an optical energy absorption density distribution that is a distribution of the product ($\mu_a \cdot \Phi$) of a light absorption coefficient and an amount of light).

In addition, the calculation unit 22 is able to analyze the second electric signals by the use of the first optical property distribution information to obtain a second optical property distribution information or an elastic property distribution. The second optical property distribution information includes an amount of light ($\Phi$) irradiated onto the light absorption material, the light absorption coefficient ($\mu_a$) of the light absorption material, and an effective scattering coefficient ($\mu_s'$). Also, the elastic property distribution is a distribution of a Grüneisen coefficient ($\Gamma$).

Thus, by using the information obtained by photoacoustic imaging for calculation or computation of an ill-posed inverse problem in an optical diffusion equation, it is possible to shorten the computing time required for solving the problem.

However, diffuse optical imaging is more advantageous in terms of quantitativity than photoacoustic imaging, though it is less advantageous in resolution. Accordingly, if the absorption coefficient distribution of low quantitativity obtained by the calculation unit 22 is used in the calculation of the inverse problem of light, it is possible to achieve imaging whose resolution is higher than that of diffuse optical imaging since the resolution is decided by the photoacoustic imaging.

The biological information imaging apparatus according to this first embodiment is constructed of the following individual components.

The light source 11 is used as a means for irradiating light of a specific wavelength that is to be absorbed by a specific one of components that constitute the living body.

The light source 11 can be composed of one or more light source components, of which at least one is designed as a light source for generating pulsed light.

That is, the light source 11 is provided with at least one pulsed light source that is capable of generating pulsed light of a period on the order of from a few nanoseconds to a few hundreds of nanoseconds. Preferably, the wavelength of the pulsed light is in the range of not less than 400 nm and not more than 1,600 nm.

A laser is preferable as the light source, but it is also possible to use a light emitting diode or the like, instead of a laser.

A variety of kinds of lasers such as a solid state laser, a gas laser, a dye laser, and a semiconductor laser can be used as the laser light source.

In this embodiment, a plurality of light sources may be used, as stated above. In that case, a plurality of light sources each generating light of an identical wavelength can be used so as to enhance the intensity of irradiation of the light to be irradiated onto the living body.

In addition, a plurality of light sources having different oscillation wavelengths may be used for measuring variation or difference in the optical property distribution depending upon the wavelengths.

Here, note that in the case of the light source 11 being composed of a single light source, if dye or OPO (Optical Parametric Oscillators) with convertible or variable wavelength to be oscillated can be used, it will be possible to measure the variation or difference in the optical property distribution according to the wavelength. It is preferred that the wavelength of the light source used be in a region from 700 nm to 1,100 nm in which the absorption of light is limited.

In a case where an optical property distribution of a tissue of the living body in the relative vicinity of a surface thereof is to be obtained, it is possible to use a wavelength region of 400 nm to 1,600 nm, for example, that is wider than the above-mentioned wavelength region.

The optical wave guide 12 of FIG. 1 plays the role of guiding the light irradiated from the light source to living body 18 that is an object to be checked. It is preferable to use optical fiber as the optical wave guide 12, but in a case where the light source 11 can be disposed in the vicinity of the living body to be checked, there will be no problem even if optical fiber is not used.

In the case of using optical fiber, it is possible to guide individual lights from a plurality of light sources to the living body surface by using a plurality of optical fibers for individual light sources, respectively, or merge lights from a plurality of light sources into a single optical fiber, thereby to guide all the lights to the living body by using only the single optical fiber.

Each of the acoustic wave detectors 13 of this embodiment detects the acoustic wave generated from the light absorption material in the living body that has absorbed a part of the energy of the light irradiated from the light source onto the living body, and converts it into a corresponding first electric signal. That is, each of the acoustic wave detectors 13 receives the acoustic wave, and outputs a first electric signal in accordance with the pressure of the acoustic wave thus received. As an acoustic wave detector 13, there can be employed a transducer using a piezo-electric phenomenon, a transducer using the resonance of light, a transducer using the change of capacitance, and so on.

Moreover, although in this embodiment, there has been shown the case where the plurality of acoustic wave detectors 13 are disposed on the living body the surface, the present invention is not limited to such an arrangement, but may include a construction that the acoustic wave can be detected in a plurality of locations.

Specifically, as long as the acoustic wave can be detected in a plurality of locations, the same effects can be obtained, so a single acoustic wave detector 13 may be scanned on the living body surface in a two-dimensional manner. Also, an area-type acoustic wave detector 13 may be provided, and the light source 11 and the area-type acoustic wave detector 13 may be arranged in opposition to the living body.

Further, when the electric signals obtained from the acoustic wave detectors 13 are small, it is preferred that the strength of each signal be amplified by the use of an amplifier. In addition, it is also desirable that an acoustic impedance matching agent for suppressing the reflection of acoustic or sound waves be used between the acoustic wave detector 13 and the living body 18 to be measured.

Each of the photodetectors 14 of this embodiment detects the optical intensity of the light 20 that is irradiated from the light source 11 to the living body and propagates in the interior of the living body, and converts it into a corresponding second electric signal. That is, each of the photodetectors 14 receives the propagation light, and outputs a second electric signal in accordance with the intensity of the propagation light thus received.

As a photodetector 14, there can be used a photodiode (PD), an avalanche photodiode (APD), a photomultiplier (PMT), and so on.

Here, note that in case where the photodetectors 14 cannot be disposed in the vicinity of the living body 18 to be checked, it is also possible to guide light to the photodetectors by the use of optical fiber.

In addition, although in this embodiment, an example using the plurality of photodetectors 14 has been shown, the present invention is not limited to such a configuration, but may include a configuration in which a single photodetector 14 can be scanned on the living body surface in a two-dimensional manner, as in the case of using the single acoustic wave detector 13. Also, an array-type photodetector 14 may be provided, and the light source 11 and the area-type photodetector 14 are arranged in opposition to each other.

The calculation unit 22 can store the intensity of the acoustic wave and the time change thereof, and convert the information thereof into data of its optical property distribution. In addition, the calculation unit 22 can store the optical intensity of the light 20, and convert it into data of its optical property distribution by means of a calculation means. Further, the calculation unit 22 performs calculation processing so as to use the data of the optical property distribution obtained by one of photoacoustic imaging or diffuse optical imaging for the other imaging. As the calculation unit 22, there can be used, for example, an oscilloscope and a computer that can analyze data stored in the oscilloscope.

Here, note that the calculation unit 22 can instead comprise a processing part in the form of a first processing unit that obtains optical property distribution information by analyzing the first electric signals, and another processing part in the form of a second processing unit that obtains optical property distribution information by analyzing the second electric signals.

In this case, the information obtained by the first information processing unit can be used for information processing in the second information processing unit, and the information obtained by the second information processing unit can be used for information processing in the first information processing unit. For example, it can be constructed such that the first information processing unit analyzes the first electric signals to obtain first optical property distribution information on the living body, after which the second information processing unit analyzes the optical property distribution information thus obtained and the second electric signals to obtain second optical property distribution information on the living body.

Here, note that in a case where light having a plurality of wavelengths is used as the light source 11, it is possible to image a concentration distribution of materials that constitute the tissue of the living body, by calculating the absorption coefficient ($\mu_a$) in the interior of the living body and the effective scattering coefficient ($\mu_s'$) for each wavelength. That is, the concentration distribution of the materials constituting the living body can be imaged by comparing the values of these optical properties and the inherent wavelength dependences of the materials, constituting the tissue of the living body, such as glucose, collagen, oxidized and reduced hemoglobin, and so on.

Furthermore, by analyzing the optical property distribution obtained from the first electric signals and the optical property distribution obtained from the second electric signals, it becomes possible to measure the elastic property distribution or Grüneisen coefficient distribution in the living body, which would be difficult to obtain in the prior art.

Specifically, the absorption coefficient ($\mu_a$) of the light absorption material is obtained from the amount of light ($\Phi$) irradiated to the light absorption material obtained by the second electric signals, and the product ($\mu_a \cdot \Phi$) of the light absorption coefficient obtained from the first electric signals and the amount of light. Then, the Grüneisen coefficient distribution is calculated by applying the sound pressure obtained from the first electric signals to the above-mentioned equation (1). Here, note that it is possible to obtain the amount of light ($\Phi$) by analyzing the second electric signals by the use of the optical property distribution obtained from the first electric signals, as stated above, or it is also possible to obtain the amount of light ($\Phi$) by analyzing only the second electric signals without using the optical property distribution.

In addition, in this embodiment of the present invention, it is desirable that an image display unit 17 be provided for displaying image information obtained by the processing of the calculation unit 22.

Embodiment 2

Next, reference will be made to a biological information imaging apparatus according to a second embodiment of the present invention.

Figure 2:
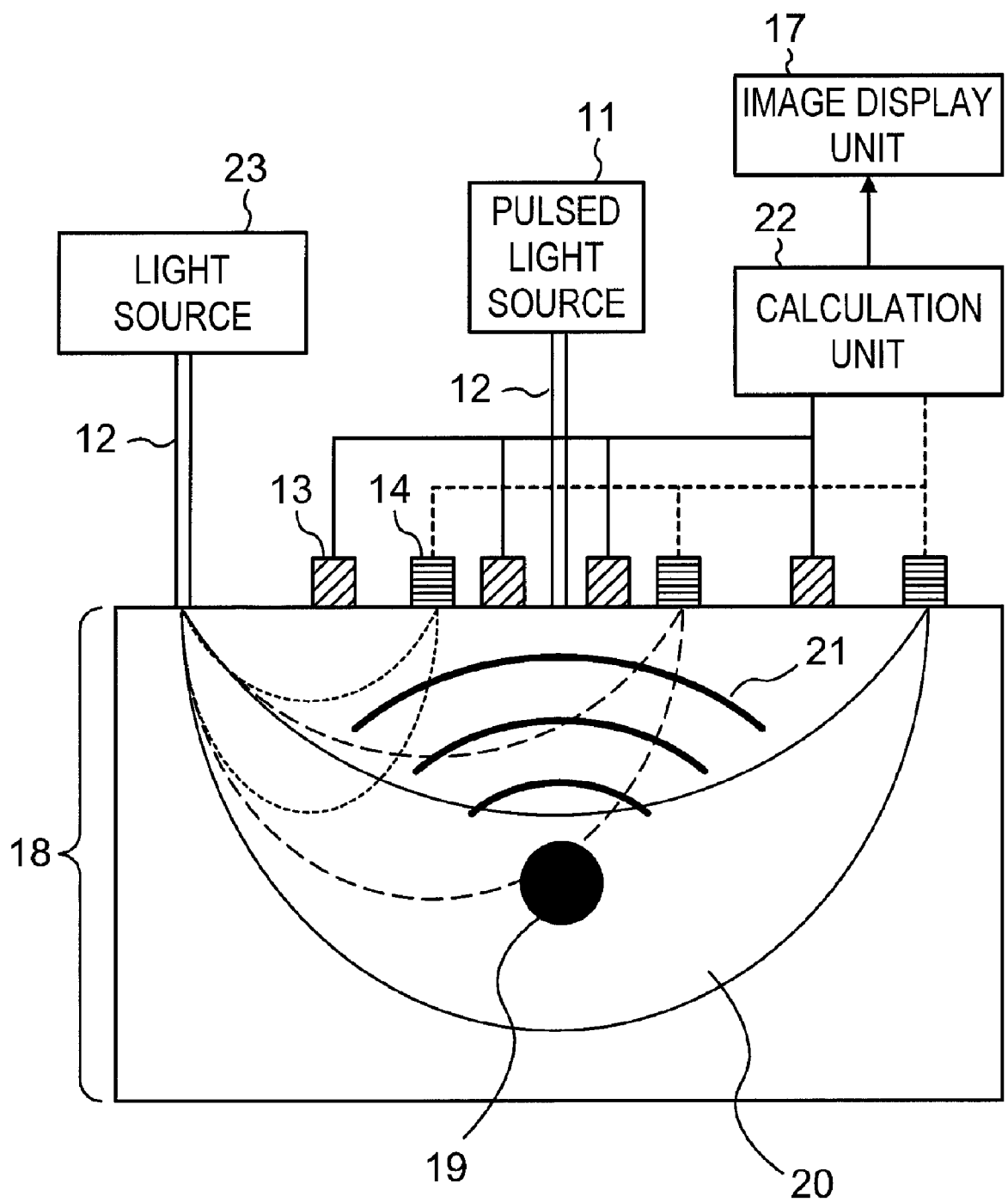
FIG. 2 is a view for explaining a constructional example of a biological information imaging apparatus in a second embodiment of the present invention.

FIG. 2 shows a view for explaining a constructional example of the biological information imaging apparatus of this second embodiment. Here, note that the same construction of this second embodiment as that of FIG. 1 is identified by the same symbols as those used in FIG. 1.

A light source in this second embodiment is composed of at least two light sources, i.e., a first light source 11 for generating pulsed light, and a second light source 23 for generating light of a waveform different from that of the pulsed light output from the first light source 11.

In addition, it is constructed such that the light irradiated from the first light source 11 onto a living body 18 can be detected and converted into first electric signals by means of a plurality of acoustic wave detectors 13, respectively, and the light irradiated from the second light source 23 onto the living body 18 can be detected and converted into second electric signals by means of a plurality of photodetectors 14, respectively.

Moreover, a calculation unit 22 is provided which serves to obtain an optical property distribution of the living body 18 by analyzing optical property distribution information, which is obtained by the analysis of the first electric signals, and the second electric signals. Here, note that this calculation unit 22 is also able to obtain an optical property distribution of the living body 18 by analyzing optical property distribution information, which is obtained by the analysis of the second electric signals, and the first electric signals.

The biological information imaging apparatus according to this second embodiment is constructed of the above-mentioned individual components.

The first light source 11 serves to irradiate pulsed light of a specific wavelength that is to be absorbed by a specific one of the components that constitute the living body.

As the first light source, it is preferable to use a laser that can generate pulsed light with a period on the order of a few nanoseconds to a few hundreds of nanoseconds, and one similar to the light source of the first embodiment can be used. Here, note that in this second embodiment, the first light source is described as being singular, but it is also possible to use a plurality of light sources for the same purpose.

Similar to the first light source 11, the second light source 23 serves to irradiate pulsed light of a specific wavelength that is to be absorbed by a specific one of components that constitute the living body.

The light generated from the second light source 23 is any of continuous light, strength modulated light, and pulsed light with a pulse width which is different from that of the pulsed light irradiated from the first pulsed light source.

In the case of using continuous light, various kinds of coherent light sources and noncoherent light sources such as semiconductor lasers, light emitting diodes, etc., can be used.

Also, as light sources for oscillating or emitting strength modulated light and pulsed light, respectively, there can be similarly used various coherent light sources and noncoherent light sources such as semiconductor lasers, light emitting diodes, etc.

Here, note that in this second embodiment, the first light source is only one, but it is also possible to use a plurality of light sources for the same purpose. For optical wave guides 12, the acoustic wave detectors 13, the photodetectors 14, and the calculation unit 22 in FIG. 2, there can be used the same ones as those of the first embodiment.

Thus, in this second embodiment, pulsed light used for photoacoustic imaging and light used for diffuse optical imaging are respectively provided separately from each other, so it is possible to obtain optical property distributions in various regions of the living body with high resolution.

Embodiment 3

Next, reference will be made to a biological information imaging apparatus according to a third embodiment of the present invention.

Figure 3:
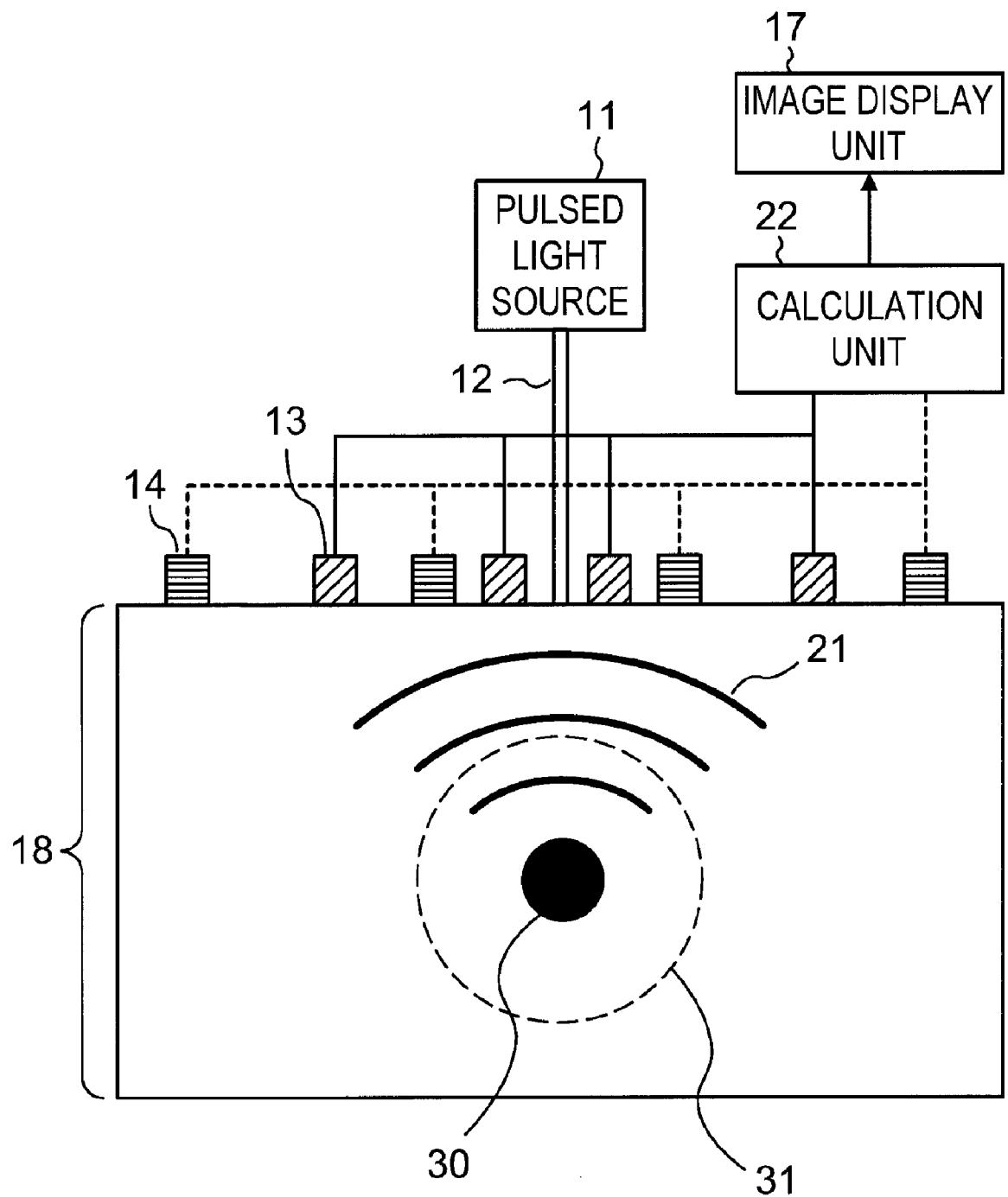
FIG. 3 is a view for explaining a constructional example of a biological information imaging apparatus in a third embodiment of the present invention.

FIG. 3 shows a view for explaining a constructional example of the biological information imaging apparatus of this third embodiment. The biological information imaging apparatus of this embodiment serves to make it possible to image the place of collection, a concentration distribution, etc., of a contrast agent introduced into a living body for the diagnosis of various diseases such as malignant tumors, Alzheimer's disease, carotid artery plaques, etc., by the use of the contrast agent.

When detecting the intensity of light having propagated in a living body, the photodetectors, serving to convert the intensity of light detected into the above-mentioned second electric signals, are constructed such that they are able to detect the optical intensity of light which is different in wavelength from the original light generated by the light source.

That is, the photodetectors are constructed such that they can detect the optical intensity of light, which has a wavelength different from that of the original light of the light source and is emitted from a light absorption material (contrast agent) in the living body that has absorbed a part of the energy of the light irradiated from the light source onto the living body.

Specifically, the biological information imaging apparatus of this embodiment is provided with a light source 11 for generating first light, and an optical wave guide 12 for guiding the first light irradiated from the light source 11 onto a living body 18.

In addition, the biological information imaging apparatus of this embodiment is also provided with a plurality of acoustic wave detectors 13. A contrast agent 30 introduced into the living body absorbs a part of the optical energy of the first light irradiated from the first light source 11 onto the living body 18 by way of the optical wave guide 12, and generates an acoustic wave 21. Each of the acoustic wave detectors 13 detects the acoustic wave 21, and converts it into a corresponding first electric signal.

Moreover, the biological information imaging apparatus of this embodiment is further provided with a plurality of photodetectors 14. The contrast agent 30 absorbs a part of the optical energy of the first light irradiated from the optical wave guide 12 onto the living body 18 thereby to generate second light 31. Each of the photodetectors 14 detects the intensity of the second light 31 after the second light has propagated in the living body, and converts it into a corresponding second electric signal.

Further, the biological information imaging apparatus of this embodiment is provided with a calculation unit 22 which serves to obtain an optical property distribution of the living body 18 by analyzing optical property distribution information, which is obtained by the analysis of the first electric signals, and the second electric signals. Here, note that this calculation unit 22 is also able to obtain an optical property distribution of the living body 18 by analyzing optical property distribution information, which is obtained by the analysis of the second electric signals, and the first electric signals.

The biological information imaging apparatus according to this third embodiment is constructed of the above-mentioned individual components.

The light source 11 of FIG. 3 irradiates pulsed light (first light) of a specific wavelength to be absorbed by the contrast agent 30 introduced into the living body 18.

As the light source 11, it is preferable to use a laser that can generate pulsed light with a period on the order of a few ns to a few hundreds of ns, and one similar to the light source of the first embodiment can be used.

Here, note that in this third embodiment, the light source 11 is described as being singular, but it is also possible to use a plurality of light sources for the same purpose.

For the optical wave guide 12, the acoustic wave detectors 13, the photodetectors 14, and the calculation unit 22 in FIG. 3, there can be used the same ones as those of the first embodiment.

Here, note that the second light 31 is generated from the contrast agent 30, and is light which has a wavelength different from that of the first light irradiated from the light source 11.

Preferably, it is desirable that the second light 31 be fluorescent light emitted from the contrast agent 30. Although indocyanine green (ICG), etc., is typically used as the contrast agent 30, any material can be used which is irradiated by pulsed light to generate an acoustic wave and at the same time to emit light having a wavelength different from that of the pulsed light.

By using such a biological information imaging apparatus as shown in this embodiment, it becomes possible to obtain and image an optical property distribution of the contrast agent introduced in the living body with higher accuracy than in the prior art.

Embodiment 4

In this fourth embodiment of the present invention, reference will be made to a biological information analyzing method according to electric signals obtained from acoustic wave detectors and photodetectors.

Figure 4:
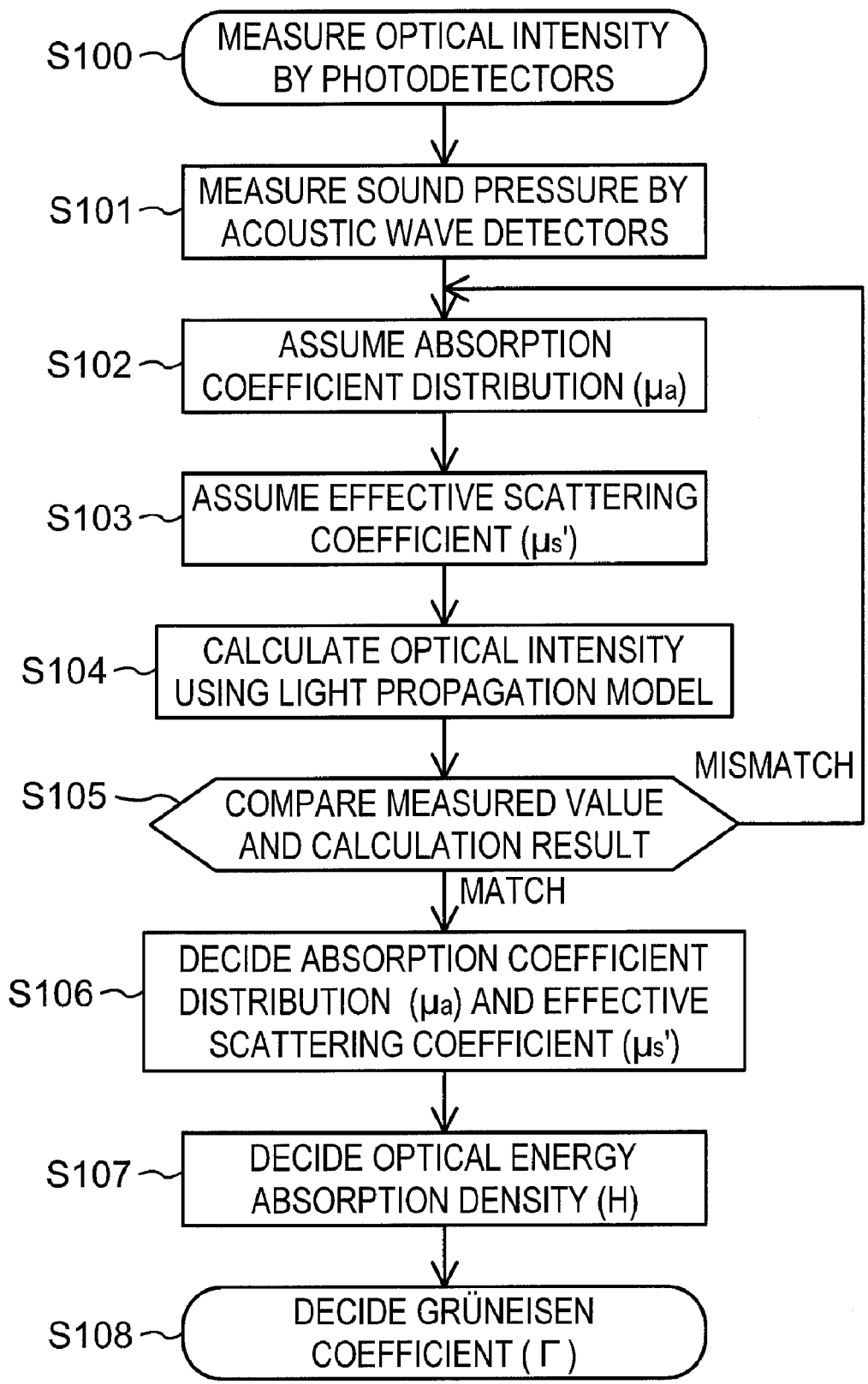
FIG. 4 shows a flow chart for explaining a biological information analyzing method according to a fourth embodiment of the present invention.

Hereinafter, reference will be made to one example of a flow chart for obtaining an absorption coefficient ($\mu_a$) and an effective scattering coefficient ($\mu_s'$), which are optical property distributions in a living body, and a Grüneisen coefficient distribution ($\Gamma$), which is an elastic characteristic of the living body, by using FIG. 4.

Each of the photodetectors detects the intensity of light 20 that has propagated in the interior of the living body, and converts it into a corresponding electric signal (S100).

Each of the acoustic wave detectors detects an acoustic wave signal generated from the light absorption material 19 lying in the living body, and converts it into a corresponding electric signal (S101).

By analyzing the electric signals obtained in step S101, the calculation unit assumes a distribution of the absorption coefficient ($\mu_a$) in the living body (S102). As stated above, the sound pressure P of a sound or acoustic wave generated from the light absorption material lying in the living body can be represented by the following expression:

$$P = \Gamma \cdot \mu_a \cdot \Phi$$

Here, $\Gamma$ is the Grüneisen coefficient; $\mu_a$ is the absorption coefficient of the light absorption material; and $\Phi$ is the amount of light irradiated onto the light absorption material.

Assuming that the Grüneisen coefficient is substantially constant in the tissue of the living body, the product of the absorption coefficient ($\mu_a$) and the amount of light ($\Phi$), i.e., the distribution of the optical energy absorption density (H), can be obtained by the time resolution measurement of the sound pressure (P). Here, the amount of light ($\Phi$) is attenuated in an exponential manner in accordance with the distance from the light source, so by appropriately assuming coefficients in an exponential function, e.g., using average values of the living body, it is possible to assume a distribution of the qualitative absorption coefficient ($\mu_a$) in the living body (S102).

In addition, the calculation unit assumes, based on the distribution of the absorption coefficient ($\mu_a$) obtained in step S102, a distribution of the effective scattering coefficient ($\mu_s'$) (S103).

By using the absorption coefficient ($\mu_a$) and the effective scattering coefficient ($\mu_s'$) assumed in steps S102, S103, respectively, the calculation unit solves a light propagation model using the radiation transport equation (Boltzmann equation) or the optical diffusion equation, and calculates an optical intensity that can be measured by each of the photodetectors (S104).

The calculation unit makes a comparison between the value of the optical intensity obtained in step S104 and the value of the optical intensity that has been actually measured in step S100 (S105). When the calculated and measured values of the optical intensity do not match with each other, a return is made to step S102, where the calculation unit assumes a new absorption coefficient ($\mu_a$) and a new effective scattering coefficient ($\mu_s'$) in the living body, and repeats this until the difference therebetween becomes sufficiently small. That is, the comparison in step S105 need not always be repeated until both of the values reach a complete match, but such a match may instead be determined based on whether the remaining difference therebetween in the calculation satisfies a convergence condition.

When in step S105, the optical intensity obtained by calculation and the optical intensity obtained by measurement match with each other, or the remaining difference therebetween in calculation satisfies the convergence condition, the calculation unit decides the assumed absorption coefficient distribution and the assumed effective scattering coefficient distribution as an absorption coefficient distribution and an effective scattering coefficient distribution in the living body (S106).

The calculation unit obtains a distribution of the amount of light ($\Phi$) by using the distributions of the absorption coefficient ($\mu_a$) and the effective scattering coefficient ($\mu_s'$) in the living body decided in step S106, and calculates the product of the absorption coefficient ($\mu_a$) in the living body and the amount of light ($\Phi$), i.e., a distribution of the optical energy absorption density (H) (S107).

The calculation unit obtains a distribution of the Grüneisen coefficient ($\Gamma$) in the living body from the magnitude of the sound pressure measured in step S101 and the distribution of the optical energy absorption density obtained in step S107 (S108).

Here, note that the sound pressure measurement in step S101 can be made earlier than the optical intensity measurement in step S100.

In addition, the assumption of the effective scattering coefficient ($\mu_s'$) in step S103 can be made earlier than the assumption of the absorption coefficient ($\mu_a$) in step S102.

Further, in case where only the absorption coefficient distribution in the living body is intended to be obtained, it is also possible to terminate the flow or process in step S106.

By performing such calculations in the calculation unit, it is possible to image the optical property distributions of the living body to be measured, such as the absorption coefficient, the effective scattering coefficient, etc., and the elastic property distribution of the living body such as the Grüneisen coefficient in an accurate manner.

In addition, by using those values, it is also possible to image the concentration distribution of materials (glucose, collagen, oxidized and reduced hemoglobin, etc.) that constitute the tissue of the living body.

Embodiment 5

Figure 5:
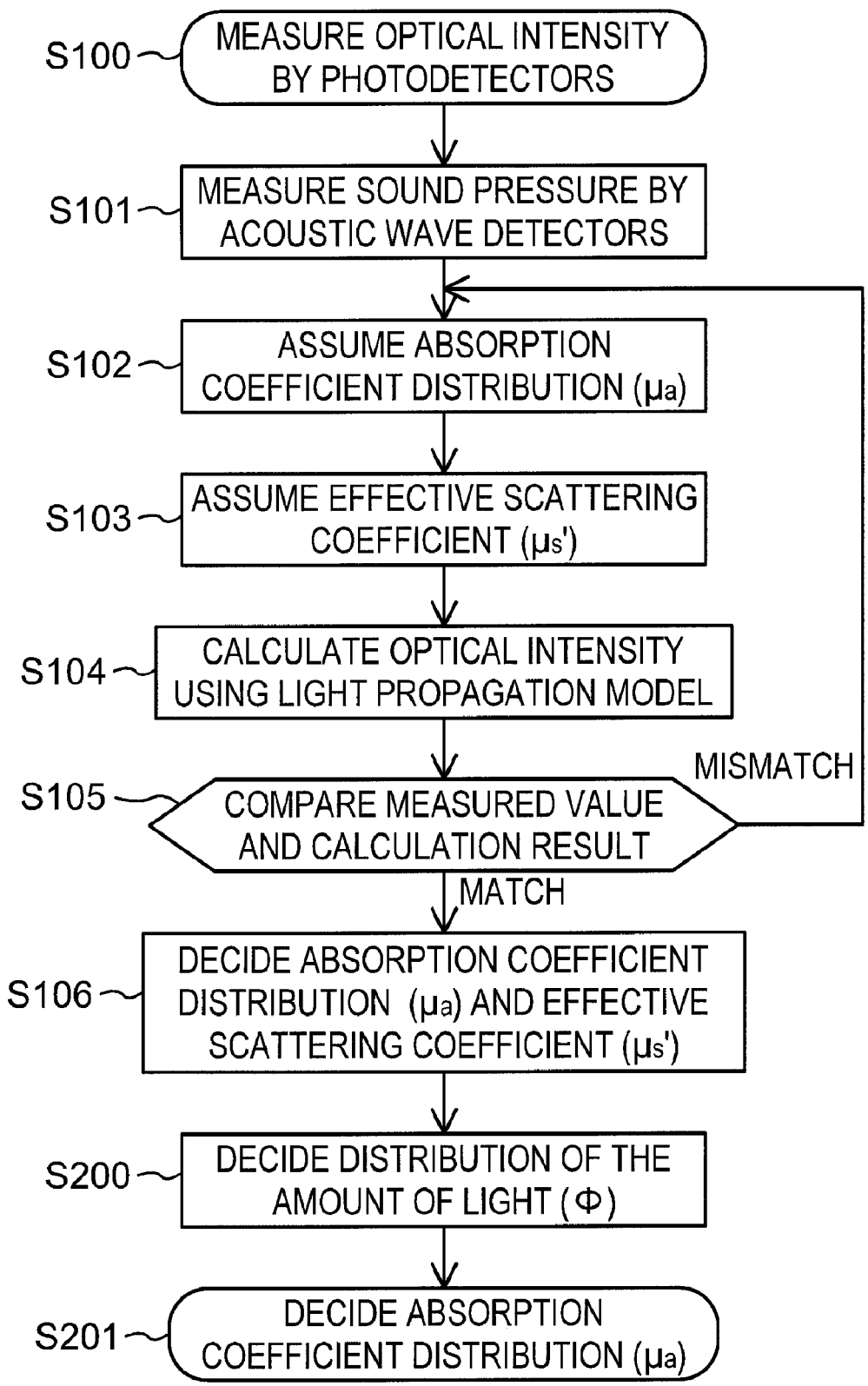
FIG. 5 shows a flow chart for explaining a biological information analyzing method according to a fifth embodiment of the present invention.

Next, reference will be made to one example of a flow chart for obtaining the distributions of the absorption coefficient ($\mu_a$) and the effective scattering coefficient ($\mu_s'$), which are optical property distributions in the living body, according to a fifth embodiment of the present invention, by using FIG. 5. Here, note that in FIG. 5, the same steps in this fifth embodiment as those in the fourth embodiment are identified by the same symbols.

The calculation unit calculates the intensities of light, which can be measured by the individual photodetectors, respectively, by solving the light propagation model according to the same processing as in the above-mentioned fourth embodiment (S104).

The calculation unit obtains the distribution of the amount of light ($\Phi$) in the living body by using the distributions of the absorption coefficient ($\mu_a$) and the effective scattering coefficient ($\mu_s'$) in the living body obtained in step S104 (S200).

The calculation unit decides the distribution of the absorption coefficient ($\mu_a$) in the living body from the magnitude of the sound pressure measured in step S101 and the distribution of the amount of light (Φ) obtained in step S200.

By performing such calculations in the calculation unit, an absorption coefficient distribution image of the living body, which is an object to be measured, can be formed in an accurate manner.

Further, by using those values, it is also possible to image the concentration distribution of materials (glucose, collagen, oxidized and reduced hemoglobin, etc.) that constitute the tissue of the living body.

Here, note that the methods described in the fourth and fifth embodiments can be achieved by using any of the apparatuses described with reference to the first through third embodiments.

Although in the above description, the amount of light (Φ) is obtained from diffuse optical imaging by using data of the acoustic wave, the distribution of the amount of light (Φ) can be obtained directly from diffuse optical imaging, and the distribution of the absorption coefficient ($\mu_a$) can be obtained by means of photoacoustic imaging.

Here, note that the methods for obtaining the absorption coefficient, the effective scattering coefficient and the Grüneisen coefficient distribution based on the above-mentioned flow charts are used here, but the present invention is not limited to these flow charts.

The gist of the present invention is to obtain optical property distributions in the interior of a living body in an accurate manner by detecting an acoustic wave generated by the absorption of energy of light irradiated from a light source to the living body, and the optical intensity of the light irradiated to the living body after the light has propagated through the interior of the living body, and by analyzing these pieces of information thus detected while making mutual use of the respective pieces of information.

Accordingly, the present invention is not limited to the flow charts described above.

Now, a biological information imaging method according to the present invention will be described below.

The gist of the inventive method resides in making the following contrivances at the time of imaging information on an object to be imaged by using distribution information on an optical property of the object to be imaged in a living body by measuring, at a plurality of locations, diffused light of the light entering the living body.

Specifically, the above-mentioned imaging is performed by using information based on an elastic wave output by the above-mentioned object to be imaged. Here, distribution information on the optical property of the object to be imaged is an absorption coefficient and/or an effective scattering coefficient. Of course, the method of imaging in the present invention does not exclude other optical properties.

Hereinafter, the present invention will be described with reference to a practical example thereof.

Example

One example of the present invention will be described. In particular, reference will be made to an example of a biological information imaging apparatus which is intended to obtain an absorption coefficient distribution of a blood vessel in a living body, by using FIG. 2.

As the light source 11, there is used a Q-switched Nd:YAG laser that can oscillate nanosecond pulsed light having a wavelength of 1,064 nm. The pulsed light generated has a pulse width of about 5 nsec and a repeat speed of 10 Hz. As the additional or second light source 23, there is used a semiconductor laser having a wavelength of 1,060 nm. At this time, the light generated by the laser is modulated at a modulation frequency of 100 MHz. In addition, the light source 23 is movable so that it can irradiate light from a plurality of positions. Here, the light source 23 is arranged such that it can irradiate light in eight places or positions.

As the acoustic wave detectors 13, there are used 256 piezo-type transducers having a center frequency of 1 MHz. The array of transducers are arranged in a two-dimensional manner.

As the photodetectors 14, there are used 8 photomultiplier tubes (PMT). In order to introduce light having propagated through the interior of the living body into the photodetectors, optical fibers (not shown in FIG. 1) are coupled to the surface of the living body so that they can guide the propagation light from the living body surface up to the photodetectors 14.

An acoustic wave signal and an optical signal converted into electric signals are respectively recorded by an oscilloscope, and are thereafter sent to a computer, and analyzed there.

If measurements are made with a specimen imitating or mimicking a blood vessel embedded in a soft tissue by using such an apparatus, it will be possible to reproduce a distribution of an absorption coefficient in a more accurate manner than with a prior art method of imaging an absorption coefficient distribution by measuring only a sound wave.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A biological information imaging apparatus comprising:
   a light source;
   an acoustic wave detector that detects an acoustic wave generated from a light absorption material in a living body that has absorbed a part of energy of light irradiated from said light source to the living body, and converts the acoustic wave into a first electric signal;
   a photodetector that detects optical intensity of a portion of the light irradiated from said light source to the living body and propagating in the living body, and converts the optical intensity into a second electric signal; and
   a calculation unit that calculates an absorption coefficient distribution of the light absorption material by applying a distribution of an amount of light irradiated to the light absorption material that is an analytical result of the second electric signal to an optical energy absorption density distribution that is an analytical result of the first electric signal.

2. The biological information imaging apparatus according to claim 1, wherein
   said calculation unit calculates an absorption coefficient distribution of the light absorption material by making use of an amount of light irradiated to the light absorption material that is an analytical result of the second electric signal for the analysis of the first electric signal.

3. The biological information imaging apparatus according to claim 1, wherein
   the light absorption material in the living body is a tumor or a blood vessel in the living body.

4. The biological information imaging apparatus according to claim 1, wherein
   said acoustic wave detector is configured to be capable of detecting an acoustic wave in a plurality of locations.

5. The biological information imaging apparatus according to claim 1, wherein said photodetector is configured to be capable of detecting the intensity of light in a plurality of locations.

6. The biological information imaging apparatus according to claim 1, wherein
said light source comprises one or more light sources, of which at least one is designed as a light source for generating pulsed light.

7. The biological information imaging apparatus according to claim 6, wherein
said light source is composed of at least two light sources which comprise a first light source for generating pulsed light, and a second light source for generating light of a waveform different from that of said pulsed light;
said acoustic wave detector is configured to be capable of converting the light irradiated from said first light source to the living body into the first electric signal; and
said photodetector is configured to be capable of converting the light irradiated from said second light source to the living body into the second electric signal.

8. The biological information imaging apparatus according to claim 1, wherein said photodetector is configured to be capable of detecting light that has a wavelength different from that of original light of said light source and is emitted from the light absorption material in the living body that has absorbed a part of energy of the light irradiated from said light source to the living body.

9. The biological information imaging apparatus according to claim 1, wherein
said light source has a wavelength in the range of not less than 400 nm and not more than 1,600 nm.

10. The biological information imaging apparatus according to claim 9, wherein
the light absorption material in the living body is a contrast agent introduced into the living body.

11. A biological information analyzing method for analyzing electric signals that are obtained from an acoustic wave detector and a photodetector, said method comprising the steps of:
the acoustic wave detector detecting an acoustic wave generated from a light absorption material in a living body that has absorbed a part of energy of light irradiated from a light source to the living body, and converting the acoustic wave into a first electric signal;
the photodetector detecting optical intensity of a portion of the light irradiated from the light source to the living body and propagating in the living body, and converting the optical intensity into a second electric signal; and
calculating an absorption coefficient distribution of the light absorption material by applying a distribution of an amount of light irradiated to the light absorption material that is an analytical result of the second electric signal to an optical energy absorption density distribution that is an analytical result of the first electric signal.

12. A biological information imaging apparatus comprising:
a light source;
an acoustic wave detector that receives an acoustic wave generated from a light absorption material in a living body that has absorbed a part of energy of light irradiated from said light source to the living body, and outputs a first electric signal in accordance with a sound pressure of the acoustic wave thus received;
a photodetector that receives propagation light of light irradiated from said light source or another light source to the living body, and outputs a second electric signal in accordance with intensity of the propagation light thus received; and
a calculation unit that calculates an absorption coefficient distribution of the light absorption material by applying a distribution of an amount of light irradiated to the light absorption material that is an analytical result of the second electric signal to an optical energy absorption density distribution that is an analytical result of the first electric signal.

13. A biological information imaging apparatus comprising:
a light source;
an acoustic wave detector that detects an acoustic wave generated from a light absorption material in a specimen that has absorbed a part of energy of light irradiated from said light source to the specimen, and converts the acoustic wave into a first electric signal;
a photodetector that detects optical intensity of a portion of the light irradiated from said light source to the specimen and propagating in the specimen, and converts the optical intensity into a second electric signal; and
a calculation unit that calculates an absorption coefficient distribution in the specimen by use of an optical energy absorption density distribution in the specimen that is obtained from the first electric signal and a distribution of an amount of light irradiated to the specimen that is obtained from the second electric signal.

14. The biological information imaging apparatus according to claim 13, wherein the light absorption material in the specimen is a tumor or a blood vessel in the specimen.

15. The biological information imaging apparatus according to claim 13, wherein said acoustic wave detector is configured to be capable of detecting an acoustic wave in a plurality of locations.

16. The biological information imaging apparatus according to claim 13, wherein said photodetector is configured to be capable of detecting the intensity of light in a plurality of locations.

17. The biological information imaging apparatus according to claim 13, wherein said light source comprises one or more light sources, of which at least one is designed as a light source for generating pulsed light.

18. The biological information imaging apparatus according to claim 17, wherein
said light source is composed of at least two light sources which comprise a first light source for generating pulsed light, and a second light source for generating light of a waveform different from that of said pulsed light;
said acoustic wave detector is configured to be capable of converting the light irradiated from said first light source to the specimen into the first electric signal; and
said photodetector is configured to be capable of converting the light irradiated from said second light source to the specimen into the second electric signal.

19. The biological information imaging apparatus according to claim 13, wherein said photodetector is configured to be capable of detecting light that has a wavelength different from that of original light of said light source and is emitted from the light absorption material in the specimen that has absorbed a part of energy of the light irradiated from said light source to the specimen.

20. The biological information imaging apparatus according to claim 13, wherein the light absorption material in the specimen is a contrast agent introduced into the specimen.

21. The biological information imaging apparatus according to claim 13, wherein said light source has a wavelength in the range of not less than 400 nm and not more than 1,600 nm.

22. A biological information analyzing method for analyzing electric signals that are obtained from an acoustic wave detector and a photodetector, said method comprising the steps of:

the acoustic wave detector detecting an acoustic wave generated from a light absorption material in specimen that has absorbed a part of energy of light irradiated from a light source to the specimen, and converting the acoustic wave into a first electric signal;

the photodetector detecting optical intensity of a portion of the light irradiated from the light source to the specimen and propagating in the specimen, and converting the optical intensity into a second electric signal; and calculating an absorption coefficient distribution in the specimen by use of an optical energy absorption density distribution in the specimen that is obtained from the first electric signal and a distribution of an amount of light irradiated to the specimen that is obtained from the second electric signal.

* * * * *